(12) United States Patent
Cuschieri et al.

(10) Patent No.: US 6,299,624 B1
(45) Date of Patent: Oct. 9, 2001

(54) HANDLE FOR A MEDICAL INSTRUMENT

(75) Inventors: Alfred Cuschieri, St. Andrews; Tim Frank, Wormit Newport-on-Tay, both of (GB); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/322,582

(22) Filed: May 27, 1999

(51) Int. Cl.$^7$ .................................................. A61B 17/32
(52) U.S. Cl. ............................ 606/167; 16/430; 200/522
(58) Field of Search ...................................... 606/167, 144, 606/147, 184, 133, 210, 205, 206, 209, 185, 188, 106, 170; 16/430, 441; 200/522, 332.2, 293.1; 29/278; 239/525; 81/415, 427.5, 177.1, 489; D8/4, 5, 107, 300, DIG. 2

(56) References Cited

U.S. PATENT DOCUMENTS

| | | | |
|---|---|---|---|
| 4,898,157 | * 2/1990 | Messroghli et al. | 606/147 |
| 5,439,474 | * 8/1995 | Li | 606/184 |
| 5,454,819 | * 10/1995 | Knoepfler | 606/147 |
| 5,728,107 | * 3/1998 | Zlock et al. | 606/139 |

* cited by examiner

Primary Examiner—Henry J. Recla
Assistant Examiner—Anthony S. King
(74) Attorney, Agent, or Firm—St.Onge Steward Johnston & Reens LLC

(57) ABSTRACT

A handle for a medical instrument comprises a first connecting means for connecting a shaft of said instrument of said handle, said shaft defining a longitudinal axis of said instrument. The handle further comprises a second connecting means for connecting a force transmission element of said instrument to said handle, said second connecting means being movable relative to said first connecting means for moving said force transmission element relative to said shaft for moving at least one tool disposed at the distal end of said shaft. The handle further comprises a first grip element and a second grip element, said first grip element and said second grip element being movable relative to each other, at least one of said first grip element and said second grip element being operatively connected with said second connecting means. Said first grip element and said second grip element are configured as shells disposed opposite to each other in symmetrical relationship with respect to said longitudinal axis of said instrument and movably by applying a counterpressure on outer gripping surfaces of said first and second grip elements.

17 Claims, 4 Drawing Sheets

HANDLE FOR A MEDICAL INSTRUMENT

BACKGROUND OF THE INVENTION

The invention generally relates to a handle for a medical instrument, such as a medical forceps for cutting or grasping tissue in the human or animal body.

The invention more particularly relates to a handle for a medical instrument, comprising a first connecting means for connecting a shaft of said instrument to said handle, said shaft defining a longitudinal axis of said instrument, further comprising a second connecting means for connecting a force transmission element of said instrument to said handle, said second connecting means being movable relative to said first connecting means for moving said force transmission element relative to said shaft for moving at least one tool disposed at the distal end of said shaft, and a first grip element and a second grip element, said first grip element and said second element being movable relative to each other, at least one of said first grip element and said second grip element being operatively connected with said second connecting means.

A handle of the afore-mentioned kind is generally known. Such a handle is generally disposed at the proximal end of the shaft of the instrument and fixed thereto by means of the first connecting means. The tool or the tools of the instrument are disposed at the distal end of the shaft.

In use of the instrument in surgery the surgeon holds the instrument in hand by gripping the two grip elements of the handle. The grip elements further have the function as actuating or operating elements for moving the tools at the distal end of the shaft. To this end the grip elements are movable relative to each other, i.e. at least one of the two grip elements is movable and the other one is immovable or stationary, or both the grip elements are movable.

At least the movable grip element is operatively connected to the second connecting means, in order to transfer a hand force applied to the movable grip element to the force transmission element and by means of the latter to the movable tool.

The most widely used type of handles comprises grip elements, which are configured in a scissors-like fashion. Such a scissors-like handle is, for example, disclosed in U.S. Pat. No. 5,810,883. The grip elements of this known handle both are configured in form of legs extending laterally at substantially right angles from the longitudinal axis of the shaft.

The two legs of the grip elements of this known handle are disposed longitudinal by one behind the other in the same plane and are movable relative to each other in that the distal leg is hinged-mounted to the proximal immovable leg. At their free ends the two legs each comprise a ring each, the ring of the proximal leg being intended for passing through the thumb and the ring of the distal leg for passing through the index or the middle finger or both.

In use in a surgical operation, this afore-mentioned handle is usually held in a position, where the legs of the grip elements stand about up-right. In this position of the handle the surgeon's hand is most relaxed, since the wrist of the hand is straight and not bent.

However, when performing a surgical operation it is often necessary to rotate the whole instrument about its longitudinal axis in order to bring the tool or tools, e.g. the jaw parts in another position at the surgical site or to a surgical site which is difficult to be accessed. Since the tool or the tools are fixed to the shaft and to the force transmission element, it is necessary in order to rotate the tools to rotate the whole instrument including the handle about the longitudinal axis of the instrument. In case of the afore-mentioned known handle this means that for rotating the instrument the legs of the grip elements must be brought into an inclined, horizontal or even a reversed up-right position.

In order to bring the instrument in such a rotated position the surgeon, therefore, must twist the wrist of his hand. Holding and simultaneously operating the grip elements in such a rotated position with a twisted or bent wrist is very difficult and cumbersome, and the surgeon's hand faster fatigues or even suffers a cramp.

The known handle, therefore, has the disadvantage that it is not sufficiently comfortable and not sufficiently ergonomic for all situations of use which may occur in surgical applications of the instrument the handle is connected to.

It is, therefore, an object of the present invention to provide a handle, which is more ergonomic and more comfortable in use, and which contributes to delaying the occurance of fatigue when working with the instrument in a wide range of working positions.

SUMMARY OF THE INVENTION

In order to achieve the afore-mentioned object the present invention provides a handle for a medical instrument, comprising a first connecting means for connecting a shaft of said instrument to said handle, said shaft defining a longitudinal axis of said instrument, further comprising a second connecting means for connecting a force transmission element of said instrument to said handle, said second connecting means being movable relative to said first connecting means for moving said force transmission element relative to said shaft for moving at least one tool disposed at the distal end of said shaft, further comprising a first grip element and a second grip element, said first grip element and said second grip element being movable relative to each other, at least one of said first grip element and said second grip element being operatively connected with said second connecting means, wherein said first grip element and said second grip element are configured as shells disposed opposite to each other in symmetrical relationship with respect to said longitudinal axis of said instrument and movable by applying a counter-pressure on outer gripping surfaces of said first and second grip elements.

The present invention provides a more ergonomic handle by the fact that the grip elements are configured as shells disposed opposite to each other in symmetrical relationship with respect to the longitudinal axis of the instrument, while the grip elements are movable by applying a counter-pressure on outer gripping surfaces of the grip elements.

The handle according to the present invention can be held in the palm of the hand like a knobstick. The shells form extended gripping surfaces lying comfortably in the hand by laying the hand around these shells. The handle according to the present invention has an enhanced symmetry with respect to the longitudinal axis of the instrument thus leaving the handling and operating conditions essentially unchanged when the handle is rotated in different angular positions. Rotational movement of the whole instrument can be thus performed by virtue of the symmetry of the handle with respect to the longitudinal axis by rotating the handle in the palm rather than by bending or twisting the wrist of the hand holding the handle as it is the case with the known handle. Thus, the handle according to the present invention reduces the drawback of rapid fatigue of the surgeon's hand holding and operating the grip elements of the handle in a surgical operation.

In a preferred embodiment said outer surfaces of said first and second grip elements are circumferentially and axially curved so that said first grip element and said second grip element form a ball-like structure.

With this particular configuration of the grip elements the handle according to the present invention has a further enhanced rotational symmetry and lies very comfortably in the surgeon's hand.

In a further preferred embodiment said first grip element is movable and said second grip element is movable.

If both the grip elements are movable, the grip elements can symmetrically be operated. The further advantage of this measure is that a larger hand force may be transferred to the force transmission element for moving the tool or tools of the instrument at the distal end thereof.

In a further preferred embodiment said first grip element is pivotably mounted about a first swivel axis, and said second grip element is pivotably mounted about a second swivel axis.

With pivotable grip elements the hand force applied by the surgeon's hand can be enhanced because the pivotable grip elements then act as levers.

In a further preferred embodiment said first and second swivel axes are disposed about centrically between a distal end and a proximal end of said first and second grip elements.

With this arrangement the grip elements can be pivoted about their respective swivel axis in two directions forward and rearward in a rocker-like fashion. Thereby movement of the tool in two directions, e.g. in case that the tools are jaw parts, which can be closed and opened, can be effected with the same power in both directions.

In a further preferred embodiment each of said first and second grip elements is pivotable about said first swivel axis and said second swivel axis, respectively, between a first end position and a second end position, and wherein said first grip element and said second grip element are preloaded via spring means towards one of said first and said second end positions.

Preloading the grip elements in one of their pivoting end positions has the advantage that the grip elements automatically move in this preloaded end position without additional external force to be applied. This preloaded end position can, for example, correspond to the closed or opened position of the tools of jaws of the instrument.

In a further preferred embodiment at least one of said first grip element and said second grip element is operatively connected to said second connecting means via a lever mechanism.

This measure advantageously contributes to an increased power transmission to the second connecting means, and, thereby to the force transmission element. In a preferred embodiment the lever mechanism is configured such that pivoting movement of the grip elements is transformed into an axial movement of the second connecting means.

Further it is preferred if said first connecting means comprises a first seat for insertion of a proximal end of said shaft therein and a first snap-in mechanism for releasably locking said shaft in said first seat.

The snap-in mechanism allows the shaft to be attached and locked to the handle and also to be released and removed from the handle very quickly and easily. The snap-in mechanism may preferably comprise a push-button which is pushed down for releasing the shaft from the handle.

In a further preferred embodiment said second connecting means comprises a second seat for insertion of a proximal end of said force transmission element therein and a second snap-in mechanism for releasably locking said force transmission element in said second seat.

Thereby the force transmission element can be also fixed and locked to the handle as well as released and removed from the handle quickly and easily.

In a further preferred embodiment the handle comprises at least a third grip element disposed between said first grip element and said second grip element and proximally extending thereof and movable with respect to said first and second grip elements.

This measure advantageously enhances the functionality of the handle according to the present invention, for example the third grip element may provide an additional input for instruments with additional degrees of freedom such as double action jaws, shaft articulation and shaft axial rotation.

In this context it is preferred if said third grip element is configured substantially cylindrical and disposed coaxially with said longitudinal axis.

Thereby the rotational symmetry of the handle according to the invention is not affected and the third grip element does not interfere with the first and second grip elements so that the first and second grip elements may be operated unaffected by the third grip element.

In a further preferred embodiment said third grip element is rotatable about said longitudinal axis and operatively connected to said shaft for rotating said shaft about said longitudinal axis.

This measure additionally enhances the rotational functioning of the whole instrument.

In a further preferred embodiment said third grip element is operatively connected to said shaft for articulating said shaft about an axis transverse to said longitudinal axis.

Thereby the handle provides an additional degree of freedom in a direction transverse to the longitudinal axis of the instrument.

In a further preferred embodiment said third grip element is operatively connected to at least one additional tool at the distal end of said shaft for moving said at least one additional tool.

Such an additional tool may be disposed at the distal end of an additional instrument which is passed through the shaft and which is operatively connected to the third grip element.

In order to enhance the rotational functioning of the handle within the surgeon's hand it is preferred, if the handle comprises at least a third grip element or a third grip element and a fourth grip element which are preferably disposed in rotationally symmetrical arrangement around said longitudinal axis.

Further features and advantages of the invention will become apparent from the following description and from the accompanying drawings.

A preferred embodiment of the invention is illustrated in the drawings and will be more fully described hereafter with reference to the drawings, in which:

DETAILED DESCRIPTION OF A PREFERRED EMBODIMENT

Figure 1:
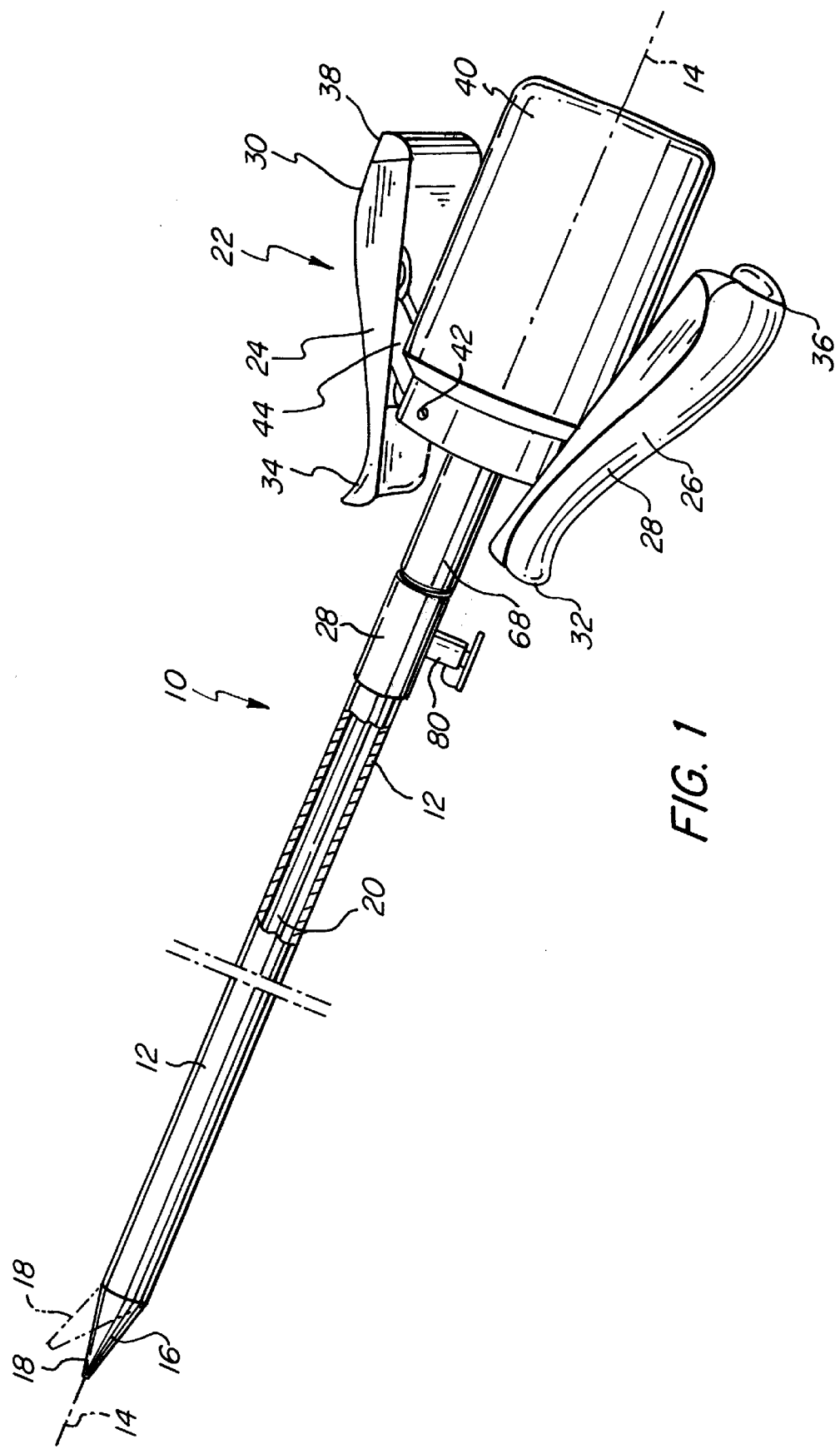
FIG. 1 is a perspective top plan view of a medical instrument having a handle according to the present invention.

In FIG. 1 a medical instrument designated with general reference numeral 10 is shown having a shaft 12 defining a longitudinal axis 14 of the instrument 10.

At a distal end of shaft 12 a first tool 16 and a second tool 18 configured as jaw parts are disposed. Tool 16 and tool 18 can be configured as cutting tools or as grasping tools.

Tool 18 is movable between a closed position and an opened position as depicted with phantom lines. Tool 16 is immovable.

Inside shaft 12 a force transmission element 20 extends from the proximal end of tool 18 and is operatively connected thereto. Force transmission element 20 is configured as a rod which is axially displacable relative to shaft 12, i.e. in the direction of longitudinal axis 14. Axial movement of force transmission element 20 relative to shaft 12 is intended to move movable tool 18, i.e. to close and open tools 16 and 18.

At a proximal end of shaft 12 a handle 22 is detachably connected to shaft 12.

Handle 22 is configured according to the present invention as will be described hereinafter.

Further with reference to FIG. 1 handle 22 comprises a first grip element 24 and a second grip element 26.

First grip element 24 and second grip element 26 are both movable.

Figure 2:
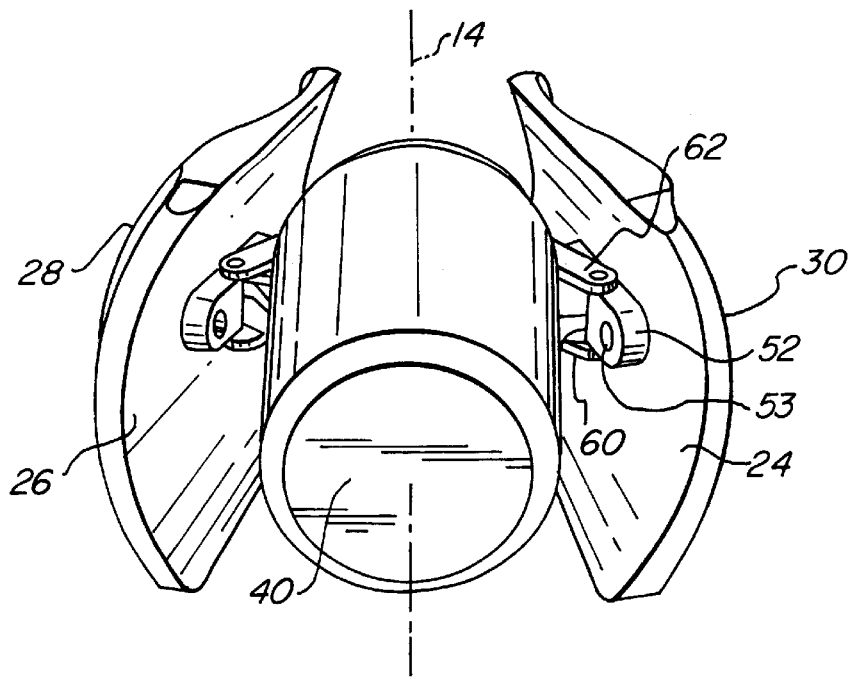
FIG. 2 is a perspective back view of the handle of FIG. 1 with this shaft removed.
Figure 3:
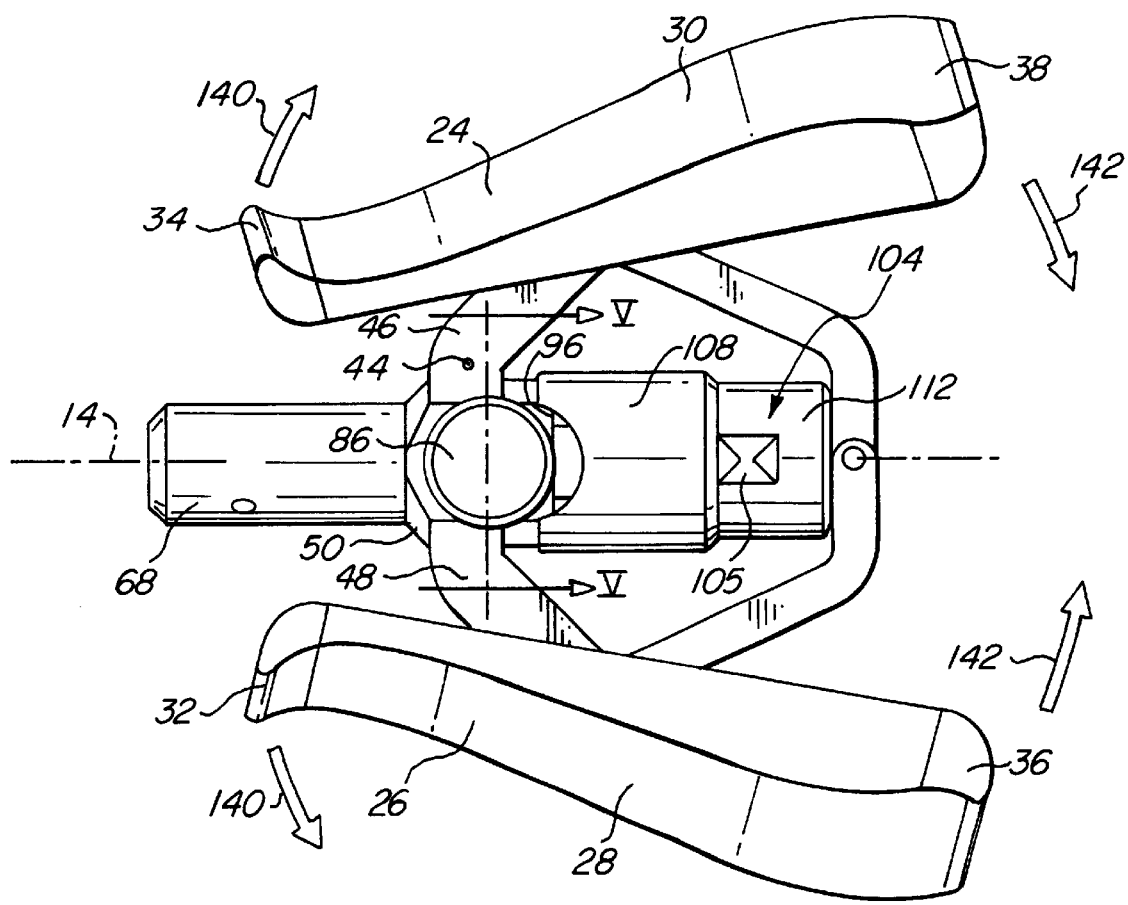
FIG. 3 is a side view of the handle, wherein a housing of the handle has been removed.

As can be seen in FIG. 1 through 3, grip elements 24 and 26 are configured as shells disposed opposite to each other in symmetrical relationship with respect to longitudinal axis 14.

Outer gripping surfaces 28 and 30 of grip elements 24 and 26 are circumferentially and axially curved. As can be seen best in FIGS. 1 and 2 grip elements 24 and 26 form a "ball-like" structure.

Distal ends 32 and 34 of grip elements 24 and 26 are curved outwardly in order to prevent the hand holding handle 22 from slipping off the handle.

Each of grip elements 24 and 26, which are preferably made of hard plastics material, has a circumferential width of about 6 cm at proximal ends 36 and 38 and of about 4 cm at distal ends 32 and 34, i.e. grip elements 24 and 26 slightly taper from proximal ends 36 and 38 to respective distal ends 32 and 34. In axial direction grip elements 24 and 26 have a length of about 6 cm. With this dimensions, which are given by way of example, handle 22 is adapted to a palm of a hand of an adult person.

Handle 22 further comprises a housing 40 coaxially disposed with respect to longitudinal axis 14. Housing 40 encases several elements of handle 22 which will be described hereinafter.

Housing 40 can be removed from handle 22 by unscrewing a fixing screw 42 which cooperates with a blind bore 44 (FIG. 3) in a first immovable arm, which carries first grip element 24, and by drawing off housing 40 towards the proximal end of handle 22.

Figure 4:
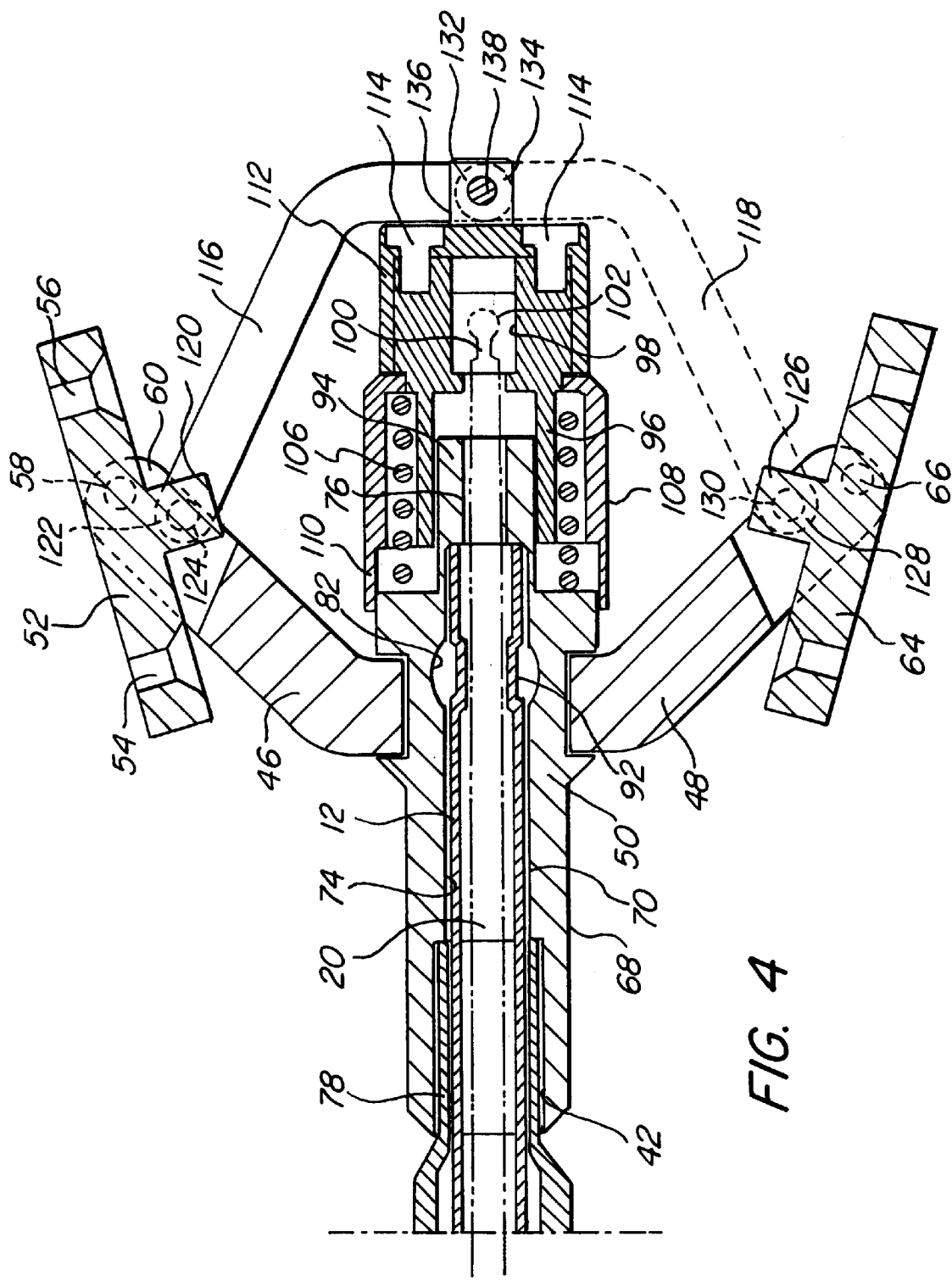
FIG. 4 is a side elevational view of a longitudinal section of the handle, with the housing removed and the grip elements omitted.

With reference to FIGS. 2 through 4 grip element 24 is mounted to first arm 46 and second grip element 26 is mounted to a second arm 48. First arm 46 and second arm 48 extend laterally and opposite to each other from a tubular body 50.

At a free end of first immovable arm 46 first grip element 24 is pivotably mounted thereto by means of a first longitudinally extending fixing element 52 to which first grip element 24 is affixed by screws (one screw 53 is shown in FIG. 2), which are passed through bores 54 and 56, respectively, into corresponding threads (not shown) in first grip element 24.

Fixing element 52 is mounted to first arm 46 pivotably about a first swivel axis 58, formed by a pin passing through legs 60 and 62 of a forked portion of first arm 46 forming the free end thereof, and through fixing element 52.

Second grip element 26 is affixed to a second arm 48 by means of a second fixing element 64 in the same manner as first grip element 24 to first arm 46 so that for a full description it may be referred to the foregoing description of the fixing of first grip element 24.

Fixing element 64 is mounted to second arm 48 pivotably about a second swivel axis 66.

First swivel axis 58 is positioned about centrally or midway between proximal end 38 and distal end 34 of first grip element 24. The same applies to second swivel axis 66 and second grip element 26. Thus, first grip element 24 and second grip element 26 can pivot about the respective swivel axes 58 and 66 in a rocker-like motion.

Further with reference to FIG. 3 and 4, tubular body 50 has a distally extending tubular extension 68 having a throughhole bore 70 having a distal portion 72 of wider diameter, a middle portion 74 of a diameter corresponding to the outer diameter of shaft 12 and a proximal portion 76 of narrower diameter corresponding to the outer diameter of force transmission element 20.

Legs 46 and 48 are monolithically connected to tubular body 50 by welding, for example.

Distal portion 72 of bore 70 is intended to hold a sleeve 78 (FIG. 1), the proximal end of which is insertable into distal portion 72 and fixed therein by means of a bayonet locking (not shown in the figures). Sleeve 78 comprises a supply 80 (FIG. 1) for introducing an irrigation fluid into shaft 12 which is passed through shaft 12 to the distal end thereof for irrigating the site of surgery.

Tubular body 50 forms a first connecting means for detachably connecting shaft 12 to handle 22.

To this end, shaft 12 is inserted through distal portion 72 of bore 70 into middle portion 74 of bore 70 which forms a seat for the proximal end of shaft 12.

Figure 5:
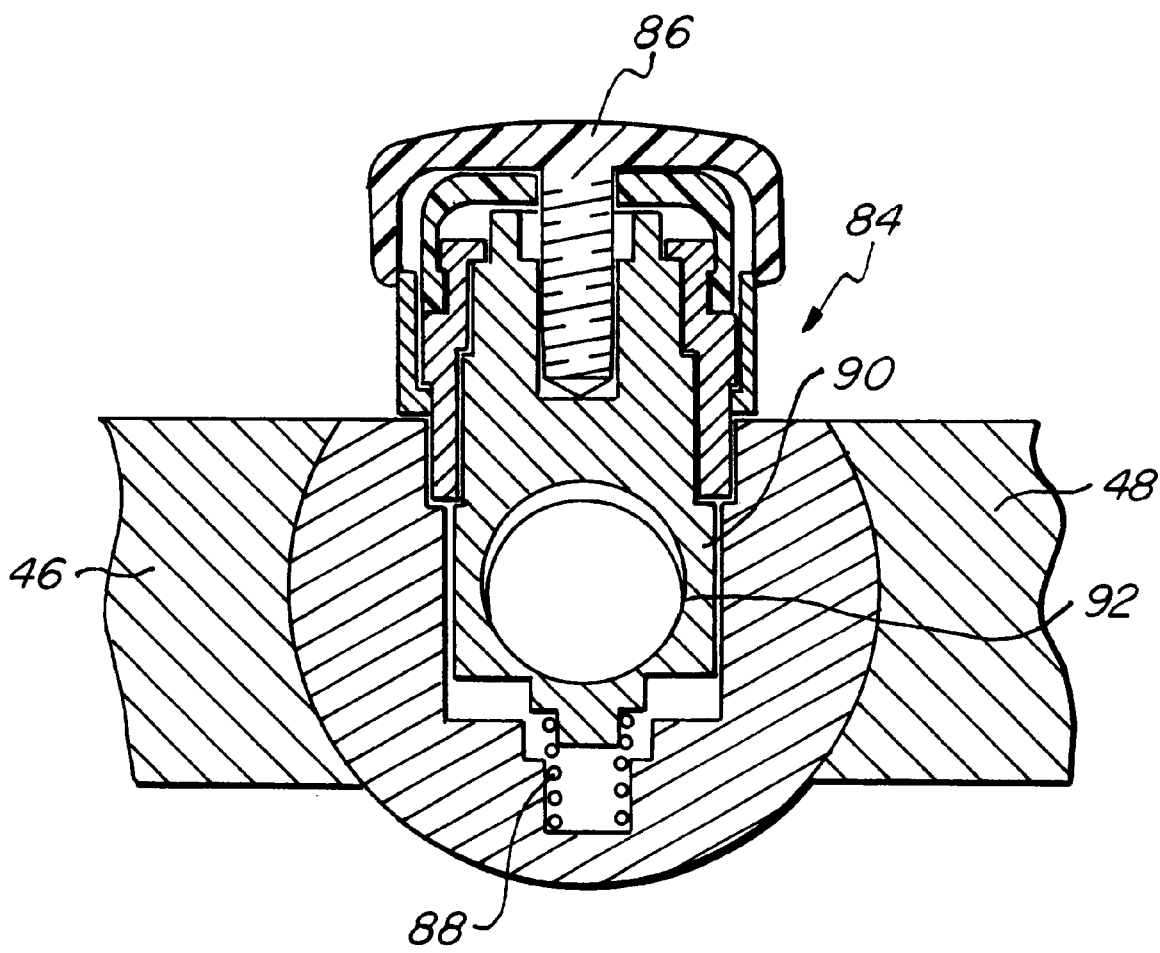
FIG. 5 is an enlarged cross-section of a detail of the handle along line V—V of FIG. 3 showing first connecting means for connecting the shaft of the instrument to the handle.

In a circular widened portion 82 of bore 70 a snap-in mechanism 84 shown in FIG. 5 is disposed for releasably locking shaft 12 to handle 22.

Snap-in mechanism 84 comprises a push-button 86 (FIGS. 3 and 5) which is preloaded by means of a spring 88 in its upper locking position.

Snap-in mechanism 84 further comprises a plate 90 inserted into bore 82 and having a circular hole 90, in which a flattened portion 92 of the proximal end shaft 12 is positioned when shaft 12 is connected to handle 22. Plate 90 cooperates with flattened portion 92 of shaft 12 for axial non-displaceably and non-rotationally fixing shaft 12 to handle 22. In the pushed-down state of push button 86 plate 90 disengages flattened portion 92 and is concentrically aligned with the proximal portion of middle portion 74 of bore 70 so that shaft 12 can be drawn out of or fully inserted into tubular body 50.

Proximal portion 76 of bore 70 is formed within a proximal extension 94 of tubular body 50. A sleeve 96 is slidably mounted on proximal extension 94 of tubular body 50.

Sleeve 96 forms a second connecting means for detachably connecting force transmission element 20 to handle 22. To this end, the proximal end of force transmission element 20 is passed through shaft 12 beyond the proximal end thereof into a bore 98 of sleeve 96.

Force transmission element 20 has at its proximal end a neck 100 less in diameter than the remaining body of force transmission element 20 and a bowl 102 at its most proximal end. Sleeve 96, i.e. bore 98, forms a seat for the proximal end of force transmission element 20, wherein a snap-in mechanism 104 (not shown in detail) cooperates with neck 100 and bowl 102 for locking force transmission element 20 to handle 22.

Snap-in mechanism 104 comprises a push-button 105, which is preloaded by means of a spring (not shown) in its upper locking position. By pushing down push-button 105 snap-in mechanism 104 is released for detachment of force transmission element 20 from handle 22.

The second connecting means in form of sleeve 96 is axially displaceable relative to the first connecting means in form of tubular body 50.

A spring 106 preloads sleeve 96 in its proximal end position shown in FIG. 4. Spring 106 is encased in a space between sleeve 96 and an outer sleeve 108 which is fixed to sleeve 96 and, therefore, is non-displaceable relative to inner sleeve 96 but is displaceable relative to tubular body 50, a distal extension 110 of outer sleeve 108 sliding on an outer surface of tubular body 50.

An end cap 112 is fixed to sleeve 96 by means of fixing screws 114.

Fixing elements 52 and 64 are connected with the second connecting means for connecting force transmission element 20 to handle 22 by a lever mechanism comprising a first lever 116 for fixing element 52 and a second lever 118 for fixing element 64.

Fixing element 52 comprises a forked protrusion 120, to which a first end 122 of first lever 116 is hinge-mounted by means of a pin 124. Fixing element 64 also comprises a forked protrusion 126 to which a first end 128 of lever 118 is hinge-mounted by means of a pin 130.

Second ends 132 and 134 of levers 116 and 118 are commonly hinge-mounted to a protrusion 136 of end cap 112 by means of a single pin 138.

The operation and function of handle 22 will be described hereinafter with reference to FIGS. 3 and 4.

At the rest state as shown in FIGS. 3 and 4, spring 106 pushes sleeve 93 and therewith second ends of levers 116 and 118 back in their proximal end position.

In this state first ends 122 and 128 of levers 116 and 118 are in their proximal end positions, too. As can be best seen in FIG. 4, in this position fixing elements 52 and 64 are tilted about their swivel axes 58 and 66, respectively, symmetrically with respect to longitudinal axis 14. In this position distal ends 32 and 34 of grip elements 24 and 26 are closer to longitudinal axis 14 than proximal ends 36 and 38 which are spaced more apart from longitudinal axis 14.

Thus, spring 106 preloads grip elements 24 and 26 in this pivoting end position.

By applying a counter pressure on outer surfaces 28 and 30 of grip elements 24 and 26 in a region proximal of swivel axes 58 and 66, grip elements 24 and 26 are pivoted about swivel axes 58 and 66, distal ends 32 and 34 of grip elements 24 and 26 thereby moving apart from longitudinal axis 14 as shown by arrows 140 and proximal ends 38 and 36 move towards longitudinal axis 14 as shown by arrows 142.

This pivoting movement about swivel axes 58 and 66 moves protrusions 120 and 126 of fixing elements 52 and 64 in distal direction, thereby pulling first ends 122 and 128 and also second ends 132 and 134 of levers 116 and 118 in distal direction, whereby sleeve 96 and, thus, force transmission element 20 axially displaces in distal direction against the load of spring 106.

When releasing the hand force grip elements 24 and 26 return by virtue of the load of spring 106 in their initial positions shown in FIGS. 1 through 4, thereby driving force transmission element 20 back in its proximal position.

The reversed pivoting movement of grip elements 24 and 26 can be supported additionally to the load of spring 106 by applying a counter pressure on outer surfaces 28 and 30 of grip elements 24 and 26 in a region distal of swivel axes 58 and 66.

In the pivoting end position of grip elements 24 and 26 shown in FIGS. 1 through 4, tools 16 and 18 may be closed so that in the other pivoting end position they are open, or vice versa.

It is to be understood that this embodiment is illustrating but not limiting the invention and that a person skilled in the art may find several modifications of the embodiment described hereinabove within the scope of the attached claims.

For example housing 40 may be configured as or replaced by a third grip element, which has substantially the same outer contour like housing 40, i.e. cylindrical and disposed coaxially with longitudinal axis 14, but movable with respect to first and second grip elements 24 and 26. The third grip element may be operatively connected to shaft 12 for rotating shaft 12 for about longitudinal axis 14 or for articulating shaft 12 about an axis (not shown) transverse to longitudinal axis 14.

Further, such a third grip element instead of housing 40 may provide an additional input for instruments which are operated by moving the third grip element.

Thus handle 22 may provide additional degrees of freedom such as moving additional tools, shaft articulation and shaft axis rotation.

Further additionally to first and second grip elements 24 and 26 at least a third, preferably a third and a fourth grip element (not shown) may be provided, having substantially the same or similar contours like first and second grip elements 24 and 26 which may be disposed in the spaces between first and second grip elements 24 and 26 so that the rotational functioning of handle 22 is further enhanced and handle 22 still more comfortably lies in the surgeon's hand.

What is claimed is:

1. A handle for a medical instrument, comprising:
   a first connecting means for connecting a shaft of said instrument to said handle, said shaft defining a longitudinal axis of said instrument;
   a second connecting means for connecting a force transmission element of said instrument to said handle, said second connecting means being movable relative to said first connecting means for moving said force transmission element relative to said shaft for moving at least one tool disposed at the distal end of said shaft;
   at least a first grip element and at least a second grip element, said first grip element and said second grip element being movable relative to each other, at least one of said first grip element and said second grip element being operatively connected with said second connecting means;

said first grip element and said second grip element each having an axial length and a circumferential width, and wherein the circumferential width, at least at a widest portion thereof, is at least as great as the axial length, such that said handle is adapted to ergonomically fit the palm of an adult; and wherein said first grip element and said second grip element are disposed opposite to each other in symmetrical relationship with respect to said longitudinal axis of said instrument and movable by applying a counter-pressure on outer gripping surfaces of said first and second grip elements.

2. The handle of claim 1, wherein said outer surfaces of said first and second grip element being circumferentially and axially curved so that said first grip element and said second grip element form a ball-like structure.

3. The handle of claim 1, wherein said first grip element is movable and said second grip element is movable.

4. The handle of claim 3, wherein said first grip element is pivotably mounted about a first swivel axis, and said second grip element is pivotably mounted about a second swivel axis.

5. The handle of claim 4, wherein said first and second swivel axis are disposed about centrically between a distal end and a proximal end of said first and second grip elements.

6. The handle of claim 5, wherein each of said first and second gripping elements is pivotable about said first swivel axis and said second swivel axis, respectively, between a first end position and a second end position, and wherein said first grip element and said second grip element are preloaded via spring means towards one of said first and said second end positions.

7. The handle of claim 6, wherein at least one of said first grip element and said second grip element is operatively connected to said second connecting means via a lever mechanism.

8. The handle of claim 1, wherein said first grip element is pivotably mounted about a first swivel axis, and said second grip element is pivotably mounted about a second swivel axis, said first and second swivel axis each being disposed laterally of the longitudinal axis, and wherein at least one of said first grip element and said second grip element is operatively connected to said second connecting means via a lever mechanism transforming a pivoting movement of said first grip element and said second grip element into an axial movement of said second connecting means.

9. The handle of claim 1, wherein said first connecting means comprises a first seat for insertion of a proximal end of said shaft therein and a first snap-in mechanism for releasably locking said shaft in said first seat.

10. The handle of claim 1, wherein said second connecting means comprises a second seat for insertion of a proximal end of said force transmission element therein and a second snap-in mechanism for releasably locking said force transmission element in said second seat.

11. The handle of claim 1, wherein it comprises at least a third grip element disposed between said first grip element and said second grip element approximately extending thereof and movable with respect to said first and second grip elements.

12. The handle of claim 11, wherein said third grip element is configured substantially cylindrical and disposed coaxially with said longitudinal axis.

13. The handle of claim 12, wherein said third grip element is rotatable about said longitudinal axis and operatively connected to said shaft for rotating said shaft about said longitudinal axis.

14. The handle of claim 1, wherein it comprises at least a third grip element disposes between said first grip element and said second grip element and proximally extending thereof and movable with respect to said first and second grip elements, and wherein said third grip element is operatively connected to said shaft for articulating said shaft about an axis transverse to said longitudinal axis.

15. The handle of claim 1, wherein it comprises at least a third grip element disposed between said first grip element and said second grip element and proximally extending thereof and movable with respect to said first and second grip elements, and wherein said third grip element is operatively connected to at least one additional tool at the distal end of said shaft for moving said at least one additional tool.

16. The handle of claim 1, wherein it comprises at least a third grip element configured as a shell and disposed circumferentially between said first and second grip elements.

17. The handle of claim 1, wherein it comprises at least a third and at least a fourth grip element, said third and fourth grip elements configured as shells, said first, second, third and fourth grip elements disposed in rotationally symmetrical arrangement around said longitudinal axis.

* * * * *